United States Patent [19]

Enomoto et al.

[11] 4,318,908
[45] * Mar. 9, 1982

[54] METHYLATED PROSTAGLANDIN DERIVATIVES

[75] Inventors: Satoru Enomoto, Fujisawa; Kiro Asano; Humio Tamura, both of Kukizaki; Hiromitsu Tanaka, Tokyo, all of Japan

[73] Assignee: Kureha Kagaku Kogyo Kabushiki Kaisha, Tokyo, Japan

[*] Notice: The portion of the term of this patent subsequent to Apr. 15, 1997, has been disclaimed.

[21] Appl. No.: 153,415

[22] Filed: May 27, 1980

[30] Foreign Application Priority Data

Dec. 6, 1979 [JP] Japan .................................. 54-158354
Mar. 19, 1980 [JP] Japan .................................. 60-35086

[51] Int. Cl.$^3$ ........................ C07J 51/00; A61K 31/56
[52] U.S. Cl. ................................. 424/243; 260/397.4; 260/397.5; 560/121
[58] Field of Search ................... 560/121; 260/397.45, 260/397.5, 397.4; 424/243

[56] References Cited
U.S. PATENT DOCUMENTS 4,198,405  4/1980  Enomoto et al. ................... 424/243

Primary Examiner—Elbert L. Roberts
Attorney, Agent, or Firm—Oblon, Fisher, Spivak, McClelland & Maier

[57] ABSTRACT

Methylated prostaglandine derivatives are steroids derivatives having at 17 position, methylated prostaglandine group such as $(Me)_2$—$PGE_2$—E
$(Me)_2$—$PGE_2$—E—2AC
$(Me)_2$—$PGE_2$—E—BA
$(Me)_2$—$PGE_2$—E—2AC—BA
$(Me)$—$PGF_2\alpha$—E
$(Me)$—$PGF_2\alpha$—E—3AC
$(Me)$—$PGF_2\alpha$—E—BA or
$(Me)$—$PGF_2\alpha$—E—3AC—BA or 600 mg/kg of the following active ingredient:
$(Me)_2$—$PGE_2'$—E
$(Me)_2$—$PGE_2'$—E—2AC
$(Me)_2$—$PGE_2'$—E—BA
$(Me)_2$—$PGE_2'$—E—2AC—BA
$(Me)$—$PGE_2$—E
$(Me)$—$PGE_2$—E—2AC
$(Me)$—$PGE_2$—E—BA or
$(Me)$—$PGE_2$—E—2AC—BA.

6 Claims, No Drawings

METHYLATED PROSTAGLANDIN DERIVATIVES

BACKGROUND OF THE INVENTION

1. Field of the Invention

The present invention relates to novel methylated prostaglandin derivatives which reduce extraordinarily side-effect maintaining superior physiological activity and preparation thereof and usages thereof.

2. Description of the Prior Arts

As it is well known, prostaglandins are found in human-body and are important physiological active compounds which impart hypotonia effect, gastric juice secretion inhibiting effect, bronchiectatic effect, blood platelet aggregation inhibiting effect or promoting effect.

Prostaglandins are abbreviated as PGs hereinafter. PGE and PGF are well known to have some special physiological activities such as hystrotrimus and yellow body degeneration, and they are useful for parturifacient, abortion at initial or middle stages of pregnancy and placental abruption after partus and control of menstrual disorder. (Brit. Med. J., 4, 618(1978), Brit. Med. J., 4 621 (1968), Amr. N.Y. Acad. Sci., 180, 456(1970); Pharmacia Vol. 9, No. 6 P. 399–402 (1973)). It is also possible to expect control of sexual cycle of female mammals, abortion and contraception.

However, the useful methylated prostaglandins cause, in its administration as a medicine, nausea, vomitting and diarrhea and also sudden variations of blood pressure, pulse and respiration. In spite of the fact that prostaglandins have been expected as useful medicines, they have been limited to only for special therapy because of serious side-effect.

The inventors have studied to develop novel methylated prostaglandin derivatives having extraordinarily reduced its side-effect.

SUMMARY OF THE INVENTION

It is an object of the present invention to provide novel methylated prostaglandin derivatives which are useful for applications of prostaglandins in higher degree by reducing extraordinarily its side-effect.

It is another object of the present invention to provide novel methylated prostaglandin derivatives which have lower side effects and are effective for longer time in comparison with conjugates of prostaglandin-steroid hormone which are previously invented.

The novel methylated prostaglandin derivatives are conjugates of methylated prostaglandin-steroid hormone having hydroxyl, acetoxy, propionyloxy, benzoyloxy or oxo group at 3-position. The conjugate of methylated prostaglandin-steroid hormone can be produced by reacting a methylated prostaglandin or an acylated methylated prostaglandin with hydroxyl group at 17- or 21-position of a steroid hormone having hydroxyl, acetoxy, propionyloxy, benzoyloxy or oxo group at 3-position by their direct reaction or by binding with a binding agent selected from the group consisting of compounds having the formula

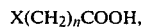

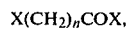

wherein n is 1 or 2 and X is a halogen atom with or without an acetylation.

DETAILED DESCRIPTION OF THE PREFERRED EMBODIMENTS

The inventors have studied to develop novel prostaglandin derivatives which are effective at a small dose and have found that the compounds having the following formula (I) are remarkably effective. The present invention has been attained by this finding.

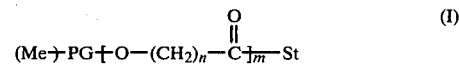

wherein (Me)-PG represents methylated $PGE_1$, $PGE_2$, $PGE_3$, $PGF_1\alpha$, $PGF_2\alpha$, $PGF_3\alpha$ or $PGE_2'$ preferably methylated $PGF_2\alpha$, $PGE_2$ or $PGE_2'$.

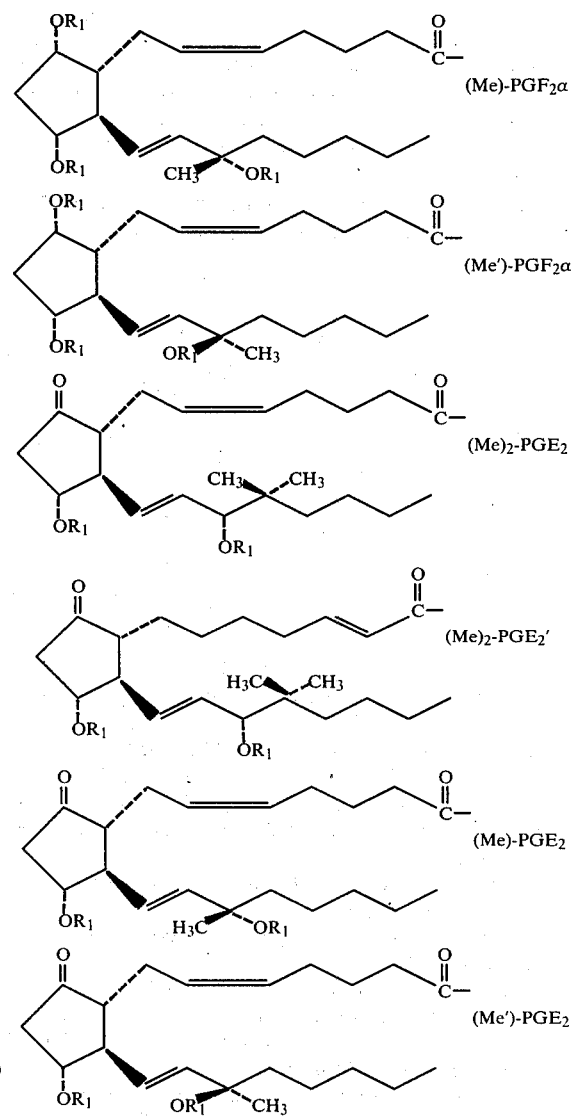

wherein $R_1$ represents hydrogen atom, acetyl, propionyl, butyryl, or benzoyl group preferably hydrogen atom or acetyl group. In the formula (I), St is selected from the group consisting of the groups having the formula (II) to (IX).

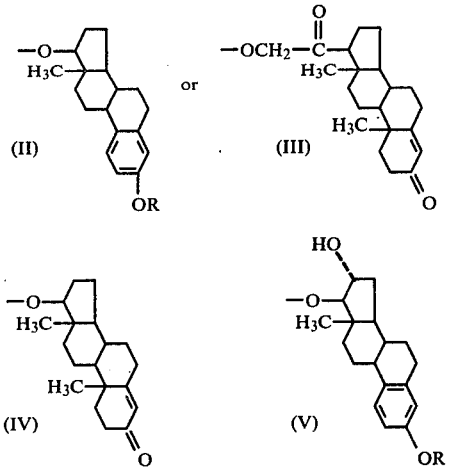

wherein R represents hydrogen atom, acetyl, propionyl, cyclopentylpropionyl, phenylpropionyl, cyclopentanepropionyl, butyryl or benzoyl group preferably hydrogen atom or benzoyl group; n is 1, 2 or 3 and m is 0 or 1.

The methylated prostaglandin derivatives having the following formula are especially preferable

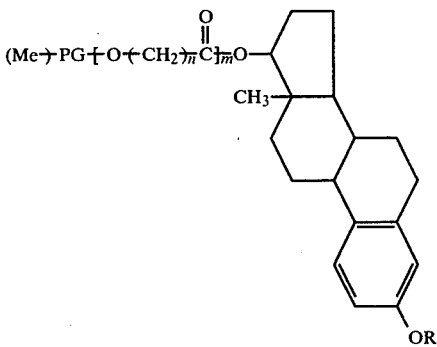

wherein R, n and m are defined above.

The typical methylated PG groups are as follows.

16,16-dimethyl-11α,15α-dihydroxy-9-oxo-5(cis)-13(trans)-prostadienoyl group ((Me)$_2$—PGE$_2$);

16,16-dimethyl-11α,15α-diacyloxy-9-oxo-5(cis)-13(trans)-prostadienoyl group (acyl group is acetyl, propionyl, butyryl or benzoyl group) ((Me)$_2$—PGE$_2$—ACY);

15β-methyl-9α,11α,15α-trihydroxy-5(cis)-13(trans)-prostadienoyl group ((Me)—PGF$_2$α);

15α-methyl-9α,11α,15β-trihydroxy-5(cis)-13(trans)-prostadienoyl group ((Me')—PGF$_2$α);

15β-methyl-9α,11α,15α-triacyloxy-5(cis)-13(trans)-prostadienoyl group (acyl group is acetyl, propionyl, butyryl or benzoyl group) ((Me)—PGF$_2$α—ACY);

15α-methyl-9α,11α,15β-triacyloxy-5(cis)-13(trans)-prostadienoyl group (acyl group is acetyl, propionyl, butyryl or benzoyl group) ((Me')—PGF$_2$α—ACY);

16,16-dimethyl-11α,15α-dihydroxy-9-oxo-2(trans)-13(trans)-prostadienoyl group ((Me)$_2$—PGE$_2$');

16,16-dimethyl-11α,15α-diacyloxy-9-oxo-2(trans)-13(trans)-prostadienoyl group (acyl group is acetyl, propionyl, butyryl or benzoyl group) ((Me)$_2$—PGE$_2$'—ACY);

15β-methyl-11α,15α-dihydroxy-9-oxo-5(cis)-13(trans)-prostadienoyl group ((Me)—PGE$_2$);

15β-methyl-11α,15α-diacyloxy-9-oxo-5(cis)-13(trans)-prostadienoyl group (acyl group is acetyl, propionyl, butyryl or benzoyl group) ((Me)—PGE$_2$—ACY);

15α-methyl-11α,15β-diacyloxy-9-oxo-5(cis)-13(trans)-prostadienoyl group (acyl group is acetyl, propionyl, butyryl or benzoyl group) ((Me')—PGE$_2$—ACY).

It is especially preferable to select (Me)$_2$—PGE$_2$, (Me)—PGF$_2$α, (Me)$_2$—PGE$_2$—ACY, (Me)—PGF$_2$α—ACY, (Me)$_2$—PGE$_2$', (Me)—PGE$_2$, (Me)$_2$—PGE$_2$—ACY or (Me)—PGE$_2$—ACY (ACY represents an acyl group).

(Me)$_2$—PGE$_2$ and (Me)—PGF$_2$α are described in CONTRACEPTION vol. 18 No. 6, page 551 to 559. December (1978). Methyl esters of (Me)$_2$—PGE$_2$', (Me)—PGE$_2$ or (Me')—PGE$_2$ are described in "Prostaglandins" (Katori, Yamamoto and Sato published by Tokyo Kodansha Mar. 1, 1979) page 220-222.

Estradiol means estradiol-17β, and estradiol-17α.

Although estradiol deivatives having estradiol group as the steroid group will be mainly illustrated, as typical compounds, the other steroid derivatives having the above-mentioned steroid group instead of estradiol group can be used.

The methylated PG and estradiol can be directly bonded and also can be bonded with a bonding agent.

The medical effects of the methylated prostaglandin derivatives of the present invention have been remarkably superior to those of the non-methylated prostaglandin derivatives. This reason should be further studied in detail and it is considered that the medical effects sustaining and the localization into uterus are simultaneously resulted.

However, when these methylated prostaglandin derivatives (I) are administrated, the characteristic side-effects of PGF$_2$α are not found and pharmacological effects such as activity for stimulating hysterotrismus, abortion, yellow body degeneration and nidation inhibiting effect are greatly imparted. Accordingly, the novel methylated prostaglandine derivatives (I) are extraordinarily effective for abortion, parturifacient, improvement for fertilization and estrus regulation contraception and menstruation facilitation.

The compounds of the present invention, the preparations thereof, the pharmacological tests, the formulation as medicines, the administration and the dose will be illustrated.

In the conjugation of estradiol and the methylated PG, it is important to bond them so as to prevent an inactivation of estradiol. On the other hand, the position of the methylated PG which is bonded to estradiol should be to prevent an inactivation of the pharmacological effects of the methylated PG.

Conjugates of prostaglandin-steroid hormone can be produced with the prostaglandin and the steroid hormone compound by their direct reaction or by using a suitable binding agent between them.

A binding agent having the formula

X(CH$_2$)$_n$COY wherein X represents a halogen atom; Y represents a halogen atom or OH group; n is 1, 2 or 3 such as monobromoacetylbromide, monochloroacetylchloride, monochloroacetic acid and monobromoacetic acid is used to react it with hydroxyl group at 17-position (inactive position) of estradiol so as to obtain an ester having the formula

X(CH₂)ₙCOOB wherein B represents a group of estradiol (hydroxyl group is eliminated) and X represents a halogen atom and then, halogen atom (X) of the ester is reacted with carboxylic acid group or its salt group of the methylated PG to obtain the product of the present invention.

The binding agent can be a compound having the formula

X(CH₂)ₙCOOH (n is 1 or 2; and X is a halogen atom) such as monochloroacetic acid, monobromoacetic acid, and monobromopropionic acid; a compound having the formula

X(CH₂)ₙCOX such as monochloroacetyl chloride and monobromoacetylbromide.

The reaction conditions will be further illustrated.

In a solvent such as tetrahydrofuran (THF), —OH group at 3-position of estradiol is converted to —ONa or —OK group by reacting with a base. The resulting product is reacted with benzoylchloride, acetylchloride, or propionylchloride in a solvent such as THF, CHCl₃ and benzene to produce the corresponding ester. Then, the binding agent having the formula

X(CH₂)ₙCOY such as monobromoacetylbromide is reacted with —OH group at 17-position of the acylated estradiol in a solvent such as dimethylsulfoxide (DMSO), dimethylformamide (DMF), pyridine, acetone and THF.

The resulting product is reacted with carboxyl group of the methylated PG in a solvent such as DMSO, DMF, pyridine, toluene, carbon tetrachloride, chloroform and THF.

When the binding agent is used the methylated PG is preferably converted into its sodium, potassium or silver salt especially silver salt before the reaction.

The reaction temperature is usually in a range of 0° to 100° C. preferably 0° to 50° C. The reaction time is usually 0.5 to 74 hours. The resulting product is purified by a conventional method to obtain the product of the present invention.

In the direct bonding, —OH group at 17-position of estradiol and —COOH group of the methylated PG are directly bonded in the presence of a catalyst such as p-toluenesulfonic acid in a solvent described above. The other steroid having the group (II) to (IX) can be used instead of estradiol to produce the corresponding product of the present invention.

The purification of the product can be carried out by a conventional method especially an elution column chromatography.

The order of the synthesis of the product of the present invention can be varied as desired. For example, the product having free OH group is produced and then, the free OH group is converted into acyloxy group.

The structures of these products are confirmed by IR spectrum, elementary analysis if necessary, UV spectrum, NMR and a melting point.

The side-effects of these products will be illustrated.

Acute toxicities (LD₅₀) of the products of the invention are measured by intravenous injections at a dose of 500 mg/kg or 600 mg/kg to ten of ICR—JCL female mice (4 week age). All of mice (10) are survived.

The tachycardia, respirogram and electrocardiogram of mice in pregnancy before and after the administration of the products of the invention are tested by a biophysiograph 180-4(4ch) (manufactured by San-ei Sokuki K. K.).

As the results, in contrast to the fact that abnormal conditions are clearly observed in the administration of (Me)—PGF₂α, any abnormal condition is not observed in case of the products of the invention.

According to these side effect tests, it is found that the products of the invention have sufficiently low toxicities and reduced side-effects.

The efficiency of abortion of the products of the invention are tested as pharmacological effects in suitable administrations and doses by using ICR—JCL pregnant mice.

As the results, the products of the invention impart greatly superior effect in comparison with that of the methylated PG.

As examples, an abortion percent is less than 10% by each subcutaneous injection of the known methylated PG at one dose of 2.4×10⁻⁸ mole/mouse, whereas an abortion percent is higher than 80% by using each of the products of the invention.

The prostaglandin derivatives (I) of the present invention can be formulated in desirable forms for injection, oral administration, intravagina administration or external application. For example, they are formulated in forms of solid compositions such as tablet, pill, powder, granules and capsule and liquid compositions such as sirup for the oral adminstration. For example, in the case of the sold compositions, starch, mannitol, cellulose, its derivatives, sorbitol, calcium carbonate, and lactose can be incorporated as a vehicle and magnesium stearate and talc can be also incorporated as a lubricant together with the product of the present invention. In the case of the liquid composition for oral administration, the product of the present invention is mixed with pharmacologically acceptable vehicle such as emulsifier, suspending agent and additive for sirup, water, alcohol, liquid paraffin and oil of olive, and also sweetening and flavour. It is possible to form a capsule by using gelatin.

In the case of the solid compositions for intravaginal administration, the product of the present invention can be mixed with wax higher fatty acid or higher alcohol which has a suitable melting point for melt in vagina and if necessary, a disintegrator having suitable viscosity.

In the case of injection, the product of the present invention is dissolved in a vegetable oil (olive oil, sesame oil, soybean oil) or is dispersed in water or a saline solution if necessary with a suitable additive such as ethanol, surfactants, emulsifiers, saline stabilizers, pH regulators and nutrients. An inclusion compound with β-dextrin can be prepared.

The concentration of the product of the present invention in the formulation is preferably 0.00001 to 10 wt.% preferably 0.0001 to 5 wt.% for injections; and 0.01 to 60 wt.% preferably 0.05 to 10 wt.% for oral compositions.

The dose of the product of the present invention is 0.001 mg to 500 mg/day/pregnant woman preferably 0.001 to 50 mg/day/pregnant woman and also a suitable dose can be determined by administrative method and condition of pregnancy.

The present invention will be further illustrated by certain examples and references which are provided for purposes of illustration only and are not intended to be limiting the present invention.

EXAMPLE 1

Preparation of estra-1,3,5(10)-triene-3-hydroxy-17β-oxy-carbonylmethyl-16,16-dimethyl-11α,15α-dihydroxy-9-oxo-5(cis)-13(trans)-prostadienoate((Me)$_2$—PGE$_2$—E)

0.1 Gram of silver 16,16-dimethyl-11α,15α-dihydroxy-9-oxo-5(cis)-13(trans)-prostadienoate (silver salt of (Me)$_2$—PGE$_2$) was dissolved into 1.5 ml. of dimethylsulfoxide (DMSO) and 0.12 g. of estra-1,3,5(10)-triene-3-hydroxy-17β-monobromoacetate was added and the reaction was carried out at 20° C. for 3 days in the dark. After the reaction, the product was purified to obtain 0.10 g. of (ME)$_2$—PGE$_2$—E.

The product was confirmed by the elementary analysis and IR spectrum.

Elementary analysis:

|  | C | H |
| --- | --- | --- |
| Calculated (%) | 72.57 | 8.55 |
| Found (%) | 72.46 | 7.96 |

IR spectrum: (cm $^{-1}$) 3420, 2920, 2850, 1735, 1705, 1610, 1580, 1490, 1442, 1378, 1350, 1280, 1216, 1142, 1076, 1042, 1020, 1000, 965, 920, 915, 865, 810, 780, 720

In the same manner, 0.15 g. of silver 16,16-dimethyl-11α,15α-diacetoxy-9-oxo-5(cis)-13(trans)-prostadienoate ((Me)$_2$—PGE$_2$—2AC) was dissolved into 1.6 ml. of DMSO and 0.14 g. of estra-1,3,5(10)-triene-3-hydroxy-17β-monobromoacetate was added and a reaction was carried out at 23° C. for 3 days. After the reaction, the product was purified to obtain 0.13 g. of estra-1,3,5(10)-triene-3-hydroxy-17β-oxycarbonylmethyl-16,16-dimethyl-11α,15α-diacetoxy-9-oxo-5(cis)-13(trans)-prostadienoate ((Me)$_2$—PGE$_2$—E—2AC).

The product was confirmed by an elementary analysis and IR spectrum.

Elementary analysis:

|  | C | H |
| --- | --- | --- |
| Calculated (%) | 70.87 | 8.14 |
| Found (%) | 70.93 | 8.06 |

IR spectrum: (cm $^{-1}$) 3400, 2920, 2850, 1735, 1705, 1580, 1500, 1440, 1370, 1230, 1145, 1080, 960, 915, 865, 812, 790, 780, 725

EXAMPLE 2

Preparation of estra-1,3,5(10)-triene-3-benzoyloxy-17β-oxycarbonylmethyl-16,16-dimethyl-11α,15α-dihydroxy-9-oxo-5(cis)-13(trans)-prostadienoate ((Me)$_2$—PGE$_2$—E—BA)

0.15 Gram of silver 16,16-dimethyl-11α,15α-dihydroxy-9-oxo-5(cis)-13(trans)-prostadienoate (Ag salt of (Me)$_2$—PGE$_2$) was added to 1.4 ml. of DMSO and 0.15 g. of estra-1,3,5(10)-triene-3-benzoyloxy-17β-monobromoacetate was added and a reaction was carried out at 25° C. for 2 days in dark. After the reaction, the product was purified to obtain 0.09 g. of (Me)$_2$—PGE$_2$—E—BA.

The product was confirmed by the elementary analysis and IR spectrum.

Elementary analysis:

|  | C | H |
| --- | --- | --- |
| Calculated (%) | 73.66 | 7.93 |
| Found (%) | 73.56 | 7.90 |

IR spectrum: (cm $^{-1}$) 3420, 3000, 2950, 2920, 2850, 1735, 1705, 1585, 1490, 1450, 1418, 1380, 1368, 1350, 1235, 1145, 1090, 1018, 965, 890, 780, 720, 700, 600

26 Milligram of the resulting (Me)$_2$—PGE$_2$—E—BA was dissolved into 0.9 ml. of anhydrous pyridine and 0.17 mg. of acetic anhydride was added and the reaction was carried out for 4 hours by cooling with ice. Then, the solvent was distilled off at 40° C. under a reduced pressure.

The residue was chromatographed on a silica gel with a mixed solvent (ethyl acetate: cyclohexane at ratio of 50:50 by volume) to obtain 22 mg. of oily estra-1,3,5(10)-triene-3-benzoyloxy-17β-oxycarbonylmethyl-16,16-dimethyl-11α,15α-diacetoxy-9-oxo-5(cis)-13(trans)-prostadinoate ((Me)$_2$—PGE$_2$—E—2AC—BA).

The product was confirmed by the elementary analysis and IR spectrum (cm $^{-1}$).

Elementary analysis:

|  | C | H |
| --- | --- | --- |
| Calculated (%) | 72.06 | 7.62 |
| Found (%) | 71.96 | 7.58 |

IR spectrum: (cm $^{-1}$) 2950, 2920, 2850, 1735, 1705, 1585, 1490, 1448, 1415, 1381, 1368, 1350, 1235, 1143, 1090, 1020, 970, 890, 780, 720, 698, 683

In the same manner, estra-1,3,5(10)-triene-3-benzoyloxy-17β-oxycarbonylmethyl-16,16-dimethyl-11α,15α-diacetoxy-9-oxo-5(cis)-13(trans)-prostadinoate was obtained.

EXAMPLE 3

Preparation of estra-1,3,5(10)-triene-3-hydroxy-17β-oxycarbonylmethyl-15β-methyl-9α,11α,15α-trihydroxy-5(cis)-13(trans)-prostadinoate ((Me)—PGF$_2$α—E)

0.1 Gram of silver 15β-methyl-9α,11α,15α-trihydroxy-5(cis)-13(trans)-prostadienoate (Ag salt of (Me)—PGF$_2$α) was dissolved into 1 ml. of DMSO and 0.12 g. of estra-1,3,5(10)-triene-3-hydroxy-17β-monobromoacetate was added and the reaction was carried out at 25° C. for 70 hours in dark. After the reaction, AgBr was separated and water was added under cooling it and the oily product was separated by a centrifugal separation. The product was dried under a reduced pressure and chromatographed on a silica gel with a mixed solvent (ethyl acetate and cyclohexane and ethanol at ratios of 45:45:10 by volume) to obtain 0.11 g. of (Me)—PGF$_2$α—E.

The product was confirmed by the elementary analysis and IR spectrum.

Elementary analysis:

|              | C     | H    |
|--------------|-------|------|
| Calculated (%) | 72.73 | 8.80 |
| Found (%)    | 72.61 | 8.65 |

IR spectrum: (cm$^{-1}$) 3400, 2920, 2850, 1735, 1610, 1580, 1495, 1440, 1378, 1350, 1280, 1215, 1140, 1075, 1040, 1020, 1000, 960, 920, 915, 865, 810, 780, 720

0.13 Gram of silver 15β-methyl-9α,11α,15α-triacetoxy-5(cis)-13(trans)-prostadienoate (Ag salt of (Me)—PGF$_2$α—3AC) was dissolved into 1.5 ml. of DMSO and 0.13 g. of estra-1,3,5(10)-triene-3-hydroxy-17β-monobromoacetate was added and the reaction was carried out at 25° C. for 3 days in dark. After the reaction, the product was purified to obtain 0.12 g. of estra-1,3,5(10)-triene-3-hydroxy-17β-oxycarbonylmethyl 15β-methyl-9α,11α,15α-triacetoxy-5(cis)-13(trans)-prostadienoate (Me)—PGF$_2$α—E—3AC.

The product was confirmed by the elementary analysis and IR spectrum.

Elementary analysis:

|              | C     | H    |
|--------------|-------|------|
| Calculated (%) | 70.33 | 8.18 |
| Found (%)    | 70.26 | 8.13 |

IR spectrum: (cm$^{-1}$) 3400, 2920, 2850, 1735, 1610, 1580, 1500, 1440, 1370, 1230, 1145, 1080, 960, 915, 865, 812, 790, 780, 725

EXAMPLE 4

Preparation of
estra-1,3,5(10)-triene-3-benzoyloxy-17β-oxycarbonyl-methyl-15β-methyl-9α,11α,15α-trihydroxy-5(cis)-13(trans)-prostadienoate ((Me)—PGF$_2$α—E—BA)

0.1 Gram of silver 15β-methyl-9α,11α,15α-trihydroxy-5(cis)-13(trans)-prostadienoate (Ag salt of (Me)—PGF$_2$α) was dissolved into 1 ml. of DMSO and 0.14 g. of estra-1,3,5(10)-triene-3-benzoyloxy-17β-monobromoacetate was added and the reaction was carried out 25° C. for 70 hours in the dark. After the reaction, AgBr was separated and water was added under cooling it and the oily product was separated by a centrifugal separation. The product was dried under a reduced pressure and chromatographed on a silica gel with a mixed solvent (ethyl acetate and cyclohexane and ethanol at ratios of 45:45:10 by volume) to obtain 0.10 g. of (Me)—PGF$_2$α—E—BA.

The product was confirmed by the elementary analysis and IR spectrum (cm$^{-1}$).

Elementary analysis:

|              | C     | H    |
|--------------|-------|------|
| Calculated (%) | 73.87 | 8.04 |
| Found (%)    | 73.72 | 8.00 |

IR spectrum: (cm$^{-1}$) 3400, 2920, 2840, 1735, 1600, 1580, 1490, 1450, 1418, 1380, 1350, 1260, 1208, 1170, 1145, 1078, 1060, 1020, 1000, 960, 910, 890, 874, 812, 796, 780, 698, 680, 610

25 Milligram of the resulting (Me)—PGF$_2$α—E—BA was dissolved into anhydrous pyridine, and then 0.20 mg. of acetic anhydride was added and the reaction was carried out by cooling with ice for 4 hours and then the solvent was distilled off under a reduced pressure at 40° C.

The residue was chromatographed on a silica gel with a mixed solvent (ethyl acetate and cyclohexane at a ratio of 50:50 by volume) to obtain 20 mg. of the oily product of estra-1,3,5(10)-triene-3-benzoyloxy-17β-oxycarbonylmethyl-15β-methyl-9α,11α,15α-triacetoxy-5(cis)-13(trans)-prostadienoate ((Me)—PGF$_2$α—E—3AC—BA).

The product was confirmed by the elementary analysis and IR spectrum (cm$^{-1}$).

Elementary analysis:

|              | C     | H    |
|--------------|-------|------|
| Calculated (%) | 71.58 | 7.59 |
| Found (%)    | 71.62 | 7.63 |

IR spectrum: (cm$^{-1}$) 2920, 2850, 1735, 1600, 1580, 1490, 1450, 1425, 1370, 1240, 1170, 1145, 1078, 1060, 965, 915, 890, 705, 680

In the same manner, estra-1,3,5(10)-triene-3-benzoyloxy-17α-oxycarbonylmethyl-15β-methyl-9α,11α,15α-triacetoxy-5(cis)-13(trans)-prostadienoate.

EXAMPLE 5

Preparation of
estra-1,3,5(10)-triene-3-hydroxy-17β-oxy-carbonyl-methyl-16,16-dimethyl-11α,15α-dihydroxy-9-oxo-2(trans)-13(trans)-prostadienoate ((Me)$_2$—PGE$_2'$—E)

0.2 Gram of silver 16,16-dimethyl-11α,15α-dihydroxy-9-oxo-2(trans)-13(trans)-prostadienoate (silver salt of (Me)$_2$—PGE$_2'$) was dissolved into 2.5 ml. of dimethylsulfoxide (DMSO) and 0.25 g. of estra-1,3,5(10)-triene-3-hydroxy-17β-monobromoacetate was added and the reaction was carried out at 20° C. for 3 days in the dark. After the reaction, the product was purified to obtain 0.20 g. of (Me)$_2$—PGE$_2'$—E.

The product was confirmed by the elementary analysis and IR spectrum.

Elementary analysis:

|              | C     | H    |
|--------------|-------|------|
| Calculated (%) | 72.83 | 8.65 |
| Found (%)    | 72.61 | 8.10 |

IR spectrum: (cm$^{-1}$) 3420, 2920, 2850, 1735, 1705, 1610, 1580, 1490, 1442, 1378, 1350, 1280, 1216, 1142, 1076, 1042, 1020, 1000, 965, 920, 915, 865, 810, 780, 720

In the same manner, 0.2 g. of silver 16,16-dimethyl-11α,15α-diacetoxy-9-oxo-2(trans)-13(trans)-prostadienoate ((Me)$_2$—PGE$_2'$—2AC) was dissolved into 2.5 ml. of DMSO and 0.2 g. of estra-1,3,5(10)-triene-3-hydroxy-17β-monobromoacetate was added and a reaction was carried out at 23° C. for 3 days. After the reaction, the product was purified to obtain 0.12 g. of estra-1,3,5(10)-triene-3-hydroxy-17β-oxycarbonylmethyl-16,16-dimethyl-11α,15α-diacetoxy-9-oxo-2(trans)-13(trans)-prostadienoate ((Me)$_2$—PGE$_2'$—E—2AC).

The product was confirmed by an elementary analysis and IR spectrum.

Elementary analysis:

|              | C     | H    |
|--------------|-------|------|
| Calculated (%) | 71.13 | 8.25 |

-continued

| | C | H |
|---|---|---|
| Found (%) | 71.02 | 8.12 |

IR spectrum: (cm$^{-1}$) 3400, 2920, 2850, 1735, 1705, 1580, 1500, 1440, 1370, 1230, 1145, 1080, 960, 915, 865, 812, 790, 780, 725

EXAMPLE 6

Preparation of
estra-1,3,5(10)-triene-3-benzoyloxy-17β-oxycarbonyl-methyl-16,16-dimethyl-11α,15α-dihydroxy-9-oxo-2(trans)-13(trans)-prostadienoate
((Me)$_2$—PGE$_2$'—E—BA)

0.15 Gram of silver 16,16-dimethyl-11α,15α-dihydroxy-9-oxo-2(trans)-13(trans)-prostadienoate (Ag salt of (Me)$_2$—PGE$_2$') was added to 2.0 ml. of DMSO and 0.15 g. of estra-1,3,5(10)-triene-3-benzoyloxy-17β-monobromoacetate was added and a reaction was carried out at 25° C. for 2 days in dark. After the reaction, the product was purified to obtain 0.09 g. of (Me)$_2$—PGE$_2$'—E—BA.

The product was confirmed by the elementary analysis and IR spectrum.

Elementary analysis:

| | C | H |
|---|---|---|
| Calculated (%) | 73.87 | 8.04 |
| Found (%) | 73.71 | 7.92 |

IR spectrum: (cm$^{-1}$) 3420, 3000, 2950, 2920, 2850, 1735, 1705, 1585, 1490, 1450, 1418, 1380, 1368, 1350, 1235, 1145, 1090, 1018, 965, 890, 780, 720, 700, 600

25 Milligram of the resulting (Me)$_2$—PGE$_2$'—E—BA was dissolved into 1.0 ml. of anhydrous pyridine and 0.20 mg. of acetic anhydride was added and the reaction was carried out for 4 hours by cooling with ice. Then, the solvent was distilled off at 40° C. under a reduced pressure.

The residue was chromatographed on a silica gel with a mixed solvent (ethyl acetate: cyclohexane at ratio of 50:50 by volume) to obtain 20 mg. of oily estra-1,3,5(10)-triene-3-benzoyloxy-17β-oxycarbonylmethyl-16,16-dimethyl-11α,15α-diacetoxy-9-oxo-2(trans)-13(trans)-prostadinoate ((Me)$_2$—PGE$_2$'—E—2AC—BA).

The product was confirmed by the elementary analysis and IR spectrum (cm$^{-1}$).

Elementary analysis:

| | C | H |
|---|---|---|
| Calculated (%) | 72.27 | 7.73 |
| Found (%) | 72.91 | 7.65 |

IR spectrum: (cm$^{-1}$) 2950, 2920, 2850, 1735, 1705, 1585, 1490, 1448, 1415, 1381, 1368, 1350, 1235, 1143, 1090, 1020, 970, 890, 780, 720, 698, 683

In the same manner, estra-1,3,5(10)-triene-3-benzoyloxy-17α-oxycarbonylmethyl-16,16-dimethyl-11α,15α-diacetoxy-9-oxo-2(trans)-13(trans)-prostadienoate was obtained.

EXAMPLE 7

Preparation of
estra-1,3,5(10)-triene-3-hydroxy-17β-oxycarbonylmethyl-15β-methyl-11α,15α-dihydroxy-9-oxo-5(cis)-13(trans)-prostadinoate ((Me)—PGE$_2$—E)

0.2 Gram of silver 15β-methyl-11α,15α-dihydroxy-9-oxo-5(cis)-13(trans)-prostadienoate (Ag salt of (Me)—PGE$_2$) was dissolved into 2 ml. of DMSO and 0.24 g. of estra-1,3,5(10)-triene-3-hydroxy-17β-monobromoacetate was added and the reaction was carried out at 25° C. for 69 hours in dark. After the reaction, AgBr was separated and water was added under cooling it and the oily product was separated by a centrifugal separation. The product was dried under a reduced pressure and chromatographed on a silica gel with a mixed solvent (ethyl acetate and cyclohexane and ethanol at ratios of 45:45:10 by volume) to obtain 0.15 g. of (Me)—PGE$_2$—E.

The product was confirmed by the elementary analysis and IR spectrum.

Elementary analysis:

| | C | H |
|---|---|---|
| Calculated (%) | 72.57 | 8.56 |
| Found (%) | 72.63 | 8.50 |

IR spectrum: (cm$^{-1}$) 3400, 2920, 2850, 1735, 1610, 1580, 1495, 1440, 1378, 1350, 1280, 1215, 1140, 1075, 1040, 1020, 1000, 960, 920, 915, 865, 810, 780, 720

0.15 Gram of silver 15β-methyl-11α,15α-diacetoxy-9-oxo-5(cis)-13(trans)-prostadienoate (Ag salt of (Me)—PGE$_2$—2AC) was dissolved into 1.5 ml. of DMSO and 0.15 g. of estra-1,3,5(10)-triene-3-hydroxy-17β-monobromoacetate was added and the reaction was carried out at 25° C. for 3 days in dark. After the reaction, the product was purified to obtain 0.13 g. of estra-1,3,5(10)-triene-3-hydroxy-17β-oxycarbonylmethyl 15β-methyl-11α,15α-diacetoxy-9-oxo-5(cis)-13(trans)-prostadienoate (Me)—PGE$_2$—E—2AC.

The product was confirmed by the elementary analysis and IR spectrum.

Elementary analysis:

| | C | H |
|---|---|---|
| Calculated (%) | 70.87 | 8.14 |
| Found (%) | 70.74 | 8.13 |

IR spectrum: (cm$^{-1}$) 3400, 2920, 2850, 1735, 1610, 1580, 1500, 1440, 1370, 1230, 1145, 1080, 960, 915, 865, 812, 790, 780, 725

EXAMPLE 8

Preparation of
estra-1,3,5(10)-triene-3-benzoyloxy-17β-oxycarbonylmethyl-15β-methyl-11α,15α-dihydroxy-9-oxo-5(cis)-13(trans)-prostadienoate ((Me)—PGE$_2$—E—BA):

0.12 Gram of silver 15β-methyl-11α,15α-dihydroxy-9-oxo-5(cis)-13(trans)-prostadienoate (Ag salt of (Me)—PGE$_2$) was dissolved into 1.5 ml. of DMSO and 0.17 g. of estra-1,3,5(10)-triene-3-benzoyloxy-17β-monobromoacetate was added and the reaction was carried out 25° C. for 70 hours in the dark. After the reaction, AgBr was separated and water was added under cooling it and the oily product was separated by a centrifugal separation. The product was dried under a reduced pressure and chromatographed on a silica gel with a mixed solvent (ethyl acetate and cyclohexane and ethanol at ratios of 45:45:10 by volume) to obtain 0.12 g. of (Me)—PGE$_2$—E—BA.

The product was confirmed by the elementary analysis and IR spectrum (cm$^{-1}$).

Elementary analysis:

|  | C | H |
|---|---|---|
| Calculated (%) | 73.66 | 7.93 |
| Found (%) | 74.62 | 7.92 |

IR spectrum: (cm$^{-1}$) 3400, 2920, 2840, 1735, 1600, 1580, 1490, 1450, 1418, 1380, 1350, 1260, 1208, 1170, 1145, 1078, 1060, 1020, 1000, 960, 910, 890, 874, 812, 796, 780, 698, 680, 610

25 Milligram of the resulting (Me)—PGE$_2$—E—BA was dissolved into anhydrous pyridine, and then 0.20 mg. of acetic anhydride was added and the reaction was carried out by cooling with ice for 4 hours and then the solvent was distilled off under a reduced pressure at 40° C.

The residue was chromatographed on a silica gel with a mixed solvent (ethyl acetate and cyclohexane at a ratio of 50:50 by volume) to obtain 20 mg. of the oily product of estra-1,3,5(10)-triene-3-benzoyloxy-17β-oxycarbonylmethyl-15β-methyl-11α,15α-diacetoxy-9-oxo-5(cis)-13(trans)-prostadienoate (Me)—PGE$_2$—E—2AC—BA.

The product was confirmed by the elementary analysis and IR spectrum (cm$^{-1}$).

Elementary analysis:

|  | C | H |
|---|---|---|
| Calculated (%) | 72.06 | 7.62 |
| Found (%) | 73.72 | 7.68 |

IR spectrum: (cm$^{-1}$) 2920, 2850, 1735, 1600, 1580, 1490, 1450, 1425, 1370, 1240, 1170, 1145, 1078, 1060, 965, 915, 890, 705, 680

In the same manner, estra-1,3,5(10)-triene-3-benzoyloxy-17α-oxycarbonylmethyl-15β-methyl-11α,15α-diacetoxy-9-oxo-5(cis)-13(trans)-prostadienoate.

Side-effect Test:

Acute toxicity (LD$_{50}$) and abnormal tachycardia, respirogram and electrocardiogram by a biophysiograph were tested.

In the measurement of LD$_{50}$, 10ICR-JCL female mice (4 week age) were used as one group. 0.2 ml of 50% ethanol-saline solution containing the drug of this invention was intravenously injected to the mice at several doses during 7 days to obtain their value of LD$_{50}$ by Litchfield-Wilcoxon graph method.

As the results, all of the mice were survived and any abnormality was not observed even in the administration of 500 mg/kg of the following active ingredient:
(Me)$_2$—PGE$_2$—E
(Me)$_2$—PGE$_2$—E—2AC
(Me)$_2$—PGE$_2$—E—BA
(Me)$_2$—PGE$_2$—E—2AC—BA
(Me)—PGF$_{2\alpha}$—E
(Me)—PGF$_{2\alpha}$—E—3AC
(Me)—PGF$_{2\alpha}$—E—BA or
(Me)—PGF$_{2\alpha}$—E—3AC—BA or 600 mg/kg of the following active ingredient:
(Me)$_2$—PGE$_2$'—E
(Me)$_2$—PGE$_2$'—E—2AC
(Me)$_2$—PGE$_2$'—E—BA
(Me)$_2$—PGE$_2$'—E—2AC—BA
(Me)—PGE$_2$—E
(Me)—PGE$_2$—E—2AC
(Me)—PGE$_2$—E—BA or
(Me)—PGE$_2$—E—2AC—BA.

The fact shows that the products had remarkably low toxicity.

Electrocardiogram was measured by a biophysiograph 180-4 (4 ch) (manufactured by San-ei Sokuki K.K.) for ICR-JCL pregnant mice (6th day) at 3 minutes after the administration of each sample.

In the test, 0.2 ml of 50% ethanol-saline solution was intravenously injected to the mice at a dose of $2.1 \times 10^{-8}$ mole per mouse. As the reference, the PGF$_{2\alpha}$ was also used as the sample (a dose of $2.1 \times 10^{-8}$ mole per mouse).

The tachycardia, respirogram and electrocardiogram of mice were tested using the following compounds:
(Me)—PGF$_{2\alpha}$—E, (Me)$_2$—PGE$_2$—E, (Me)—PGF$_{2\alpha}$—E—BA, (Me)—PGE$_2$, (Me)—PGE$_2$—E, (Me)$_2$—PGE'$_2$—E, and (Me)—PGE$_2$—E—BA.

The tachycardia, respirogram and electrocardiogram after the administration of (Me)—PGF$_{2\alpha}$ or (Me)—PGE$_2$—E—BA are abnormally different from those of the products of the invention. The tachycardia, respirogram and electrocardiogram after the administration of the products of the invention are normal. Accordingly, the products of the invention are advantageous medicines since they do not cause any abnormal effects.

| Composition: | | |
|---|---|---|
| Formula 1 | | |
| (ME)—PGF$_{2\alpha}$—E—BA | 0.5 | wt. parts |
| Mannitol | 35 | wt. parts |
| Carboxymethyl cellulose | 5 | wt. parts |
| Magnesium stearate | 5 | wt. parts |
| Sorbitol | 25 | wt. parts |
| Talc. | 30 | wt. parts |

The components were mixed and pulverized and compressed to form a tablet having a diameter of 10 mm.

| Formula 2 | | |
|---|---|---|
| (Me)$_2$—PGE$_2$—E | 0.05 | wt. parts |
| Nonionic surfactant | 2.0 | wt. parts |
| Ethanol | 30 | wt. parts |
| Physiological NaCl solution | 95 | wt. parts |

The components were heated and mixed and sterilized to prepare an injection.

Test of abortion (subcutaneous injection):

Each of the active ingredients shown in the following table was dissolved in olive oil. After each of the solution of the active ingredient was given to the ICR mice of four day of pregnancy (10 mice as one group) by subcutaneous injection only once and their breeding were continued to observe them until the expected partus. Each efficiency of abortion was measured under the consideration of effect of abortion. The results are shown in Table.

TABLE

| Sample | Dose (mole/mouse) | Efficiency of abortion (%) |
|---|---|---|
| (Me)$_2$—PGE$_2$ | 2.4 × 10$^{-8}$ | 0 |
| (Me)—PGF$_2$α | " | 0 |
| (Me)$_2$—PGE$_2$—E | " | 80 |
| (Me)$_2$—PGE$_2$—E—BA | " | 100 |
| (Me)$_2$—PGE$_2$—E—2AC | " | 100 |
| (Me)$_2$—PGE$_2$' | 2.0 × 10$^{-8}$ | 0 |
| (Me)—PGE$_2$ | " | 0 |
| (Me)$_2$—PGE$_2$'—E | " | 100 |
| (Me)$_2$—PGE$_2$'—E—BA | " | 100 |
| (Me)$_2$—PGE$_2$'—E—2AC | " | 80 |

We claim:

1. Methylated prostaglandin derivatives having the formula (I)

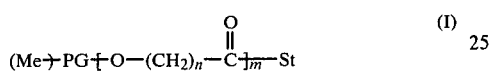

wherein (ME)—PG represents methylated PGE$_1$, PGE$_2$, PGE$_3$, PGF$_1$α, PGF$_2$α, PGF$_3$α or PGE$_2$' preferably methylated PGF$_2$α, PGE$_2$ or PGE$_2$'.

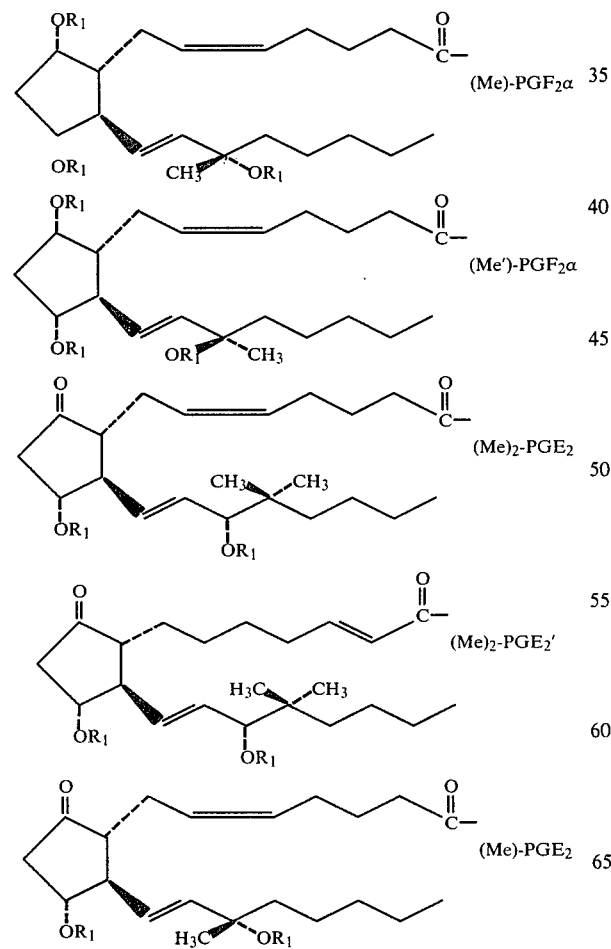

wherein R$_1$ represents hydrogen atom, acetyl, propionyl, butyryl, or benzoyl group preferably hydrogen atom or acetyl group. In the formula (I), St is selected from the group consisting of the groups having the formula (II) to (IX).

wherein R represents hydrogen atom, acetyl, propionyl, cyclopentylpropionyl, phenylpropionyl, cyclopentanepropionyl, butyryl or benzoyl group preferably hydrogen atom or benzoyl group; n is 1, 2 or 3 and m is 0 or 1.

2. Methylated prostaglandin derivatives having the formula wherein R, n and m are defined in claim 1.

3. Methylated prostaglandin derivatives selected from the group consisting of
16,16-dimethyl-11α,15α-dihydroxy-9-oxo-5(cis)-13(trans)-prostadienoyl group ((Me)$_2$—PGE$_2$);
16,16-dimethyl-11α,15α-diacyloxy-9-oxo-5(cis)-13(trans)-prostadienoyl group (acyl group is acetyl, propionyl, butyryl or benzoyl group) ((Me)$_2$—PGE$_2$—ACY);

15β-methyl-9α,11α,15α-trihydroxy-5(cis)-13(trans)-prostadienoyl group ((Me)—PGF₂α);

15α-methyl-9α,11α,15β-trihydroxy-5(cis)-13(trans)-prostadienoyl group ((Me')—PGF₂α);

15β-methyl-9α,11α,15α-triacyloxy-5(cis)-13(trans)-prostadienoyl group (acyl group is acetyl, propionyl, butyryl or benzoyl group) ((Me)—PGF₂α—ACY);

15α-methyl-9α,11α,15β-triacyloxy-5(cis)-13(trans)-prostadienoyl group (acyl group is acetyl, propionyl, butyryl or benzoyl group) ((Me')—PGF₂α—ACY);

16,16-dimethyl-11α,15α-dihydroxy-9-oxo-2(trans)-13(trans)-prostadienoyl group ((Me)₂—PGE₂');

16,16-dimethyl-11α,15α-diacyloxy-9-oxo-2(trans)-13(trans)-prostadienoyl group (acyl group is acetyl, propionyl, butyryl or benzoyl group) ((Me)₂—PGE₂'—ACY);

15β-methyl-11α,15α-dihydroxy-9-oxo-5(cis)-13(trans)-prostadienoyl group ((Me)—PGE₂);

15β-methyl-11α,15α-diacyloxy-9-oxo-5(cis)-13(trans)-prostadienoyl group (acyl group is acetyl, propionyl, butyryl or benzoyl group) ((Me)—PGE₂—ACY);

15α-methyl-11α,15β-diacyloxy-9-oxo-5(cis)-13(trans)-prostadienoyl group (acyl group is acetyl, propionyl, butyryl or benzoyl group) ((Me')—PGE₂—ACY).

4. An abortifacient which comprises prostaglandin derivative according to claim 1 in combination with an inert pharmacologically acceptable carrier.

5. A parturifacient which comprises prostaglandin derivative according to claim 1 in combination with an inert pharmacologically acceptable carrier.

6. A contraceptive agent which comprises prostaglandin derivative according to claim 1 in combination with an inert pharmacologically acceptable carrier.

* * * * *